United States Patent
Tsuji et al.

(10) Patent No.: US 10,174,386 B2
(45) Date of Patent: Jan. 8, 2019

(54) METHOD OF QUANTITATIVELY ANALYZING MICROORGANISM TARGETING RRNA

(75) Inventors: Hirokazu Tsuji, Minato-ku (JP); Kazunori Matsuda, Minato-ku (JP); Takashi Asahara, Minato-ku (JP); Koji Nomoto, Minato-ku (JP); Mayumi Kiwaki, Minato-ku (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 737 days.

(21) Appl. No.: 11/814,579

(22) PCT Filed: Jan. 30, 2006

(86) PCT No.: PCT/JP2006/301467
§ 371 (c)(1),
(2), (4) Date: Jul. 24, 2007

(87) PCT Pub. No.: WO2006/080501
PCT Pub. Date: Aug. 3, 2006

(65) Prior Publication Data
US 2009/0170078 A1 Jul. 2, 2009

(30) Foreign Application Priority Data
Jan. 31, 2005 (JP) ................... 2005-023448

(51) Int. Cl.
| C12Q 1/68 | (2018.01) |
| C12Q 1/689 | (2018.01) |
| C12Q 1/6844 | (2018.01) |
| C12Q 1/6851 | (2018.01) |

(52) U.S. Cl.
CPC ........... *C12Q 1/689* (2013.01); *C12Q 1/6844* (2013.01); *C12Q 1/6851* (2013.01)

(58) Field of Classification Search
USPC .................. 435/6, 6.12; 536/24.33
See application file for complete search history.

(56) References Cited

U.S. PATENT DOCUMENTS

| 6,602,663 B1 | 8/2003 | Kawai et al. |
| 2003/0077601 A1 | 4/2003 | Ebersole et al. |
| 2004/0072242 A1* | 4/2004 | Hunter et al. ................. 435/7.1 |
| 2004/0076990 A1* | 4/2004 | Picard .................... C07H 21/04 435/6.12 |
| 2004/0110247 A1* | 6/2004 | Moreillon et al. .............. 435/32 |
| 2005/0266468 A1* | 12/2005 | Bedzyk et al. .................... 435/6 |

FOREIGN PATENT DOCUMENTS

| CN | 1154410 A | 7/1997 |
| EP | 1 431 400 A2 | 6/2004 |
| EP | 1 431 400 A3 | 6/2004 |
| JP | 10-210980 | 8/1998 |
| JP | 10-248600 | 9/1998 |
| JP | 2001-112485 | 4/2001 |
| JP | 2002-238585 | 8/2002 |
| JP | 2003-259879 | 9/2003 |
| JP | 2004 504069 | 2/2004 |
| WO | WO00/17395 | 3/2000 |
| WO | WO 2004/015141 A2 | 2/2004 |
| WO | WO 2004/015141 A3 | 2/2004 |
| WO | 2004/044247 | 5/2004 |

OTHER PUBLICATIONS

Christensen, H et al. Phylogenetic relationships of *Salmonella* based on rRNA sequences. Int.J. Syst. Bacteriol., vol. 48, pp. 605-610, 1998.*

Centurion-Lara, A et al. Detection of treponema pallidum by a sensitive reverse transcriptase PCR. J. Clin. Microbiol., vol. 35, No. 6, pp. 1348-1352, 1997.*

Fey, A et al. Establishment of a real-time PCR-based approach for accurate quantitation of bacterial RNA targets in water, using *Salmonella* as a model organism. Applied and Environmental Microbiology, Vil. 70, No. 6, pp. 3618-3623, Jun. 2004.* van Beckhoven, J.R.C.M. et al. Detection of *Clavibacter michiganensis* subsp. *sepedonicus* by AmpliDet RNA, a new technology based on real time monitoring of NASBA amplicons with a molecular beacon. Journal of Applied Microbiology, vol. 93, p. 840-849, 2002.*

Stults, J.R. et al. Application of the 5' Flurogenic exonuclease assay (TaqMan) for quantitative ribosomal DNA and rRNA analysis in sediments. Applied and Environmental Microbiology, vol. 67(6). p. 2781-2789, 2001.*

Rokbi, B, et al al. Assesment of Helicobacter pylori gene expression within mouse and human gastric mucosae by real-time reverse transcriptase PCR. Infection and Imuunity, vol. 69, No. 8, p. 4759-4766, 2001.*

Moeseneder, M et al. Horizontal and vertical complexity of attached and free-living bacteria of the eastern mediterranean sea, determined by 16srDNA and 16S rRNA fingerprints. Limnol. Oceanogr., vol. 46(1), p. 95-107, 2001.*

Felske, A et al. Quantitation of 16S rRNAs in complex bacterial communities by multiple competitive reverse transcription-PCR in temperature gradient gel electrophoresis fingerprints. Applied and Environ. Microbiol., Vo. 64 (11), p. 4581-4587, 1998.*

Nadkarni MA. et al. Determination of bacterial load by real-time PCR using a broad-range (universal) probe and primers set. Microbiology, vol. 148, p. 257-266, 2002.*

(Continued)

*Primary Examiner* — Suryaprabha Chunduru
(74) *Attorney, Agent, or Firm* — Oblon, McClelland, Maier & Neustadt, L.L.P.

(57) ABSTRACT

An object of the present invention is to provide a method of quantitating or detecting a microorganism, capable of detecting a live microorganism at high sensitivity and more precisely. A method of quantitating a microorganism of interest, using as an index the amount of rRNA of the microorganism of interest is provided.

13 Claims, 4 Drawing Sheets

Specification includes a Sequence Listing.

(56) References Cited

OTHER PUBLICATIONS

Kumar, KA. et al. Quantitative plasmodium sporozoite neutralization assay (TSNA). J Immunol Methods, vol. 292, p. 157-164, 2004.*
Dreier, J. et al. Two novel real-time transcriptase PCR assay for rapid detection of bacterial contamination in platelet concentrations. J Clin Microbiol., vol. 42(10), p. 4759-4764, 2004.*
Labrenz, M. et al. Development and application of a real-time PCR approach for quantitation of uncultured bacteria in the central Baltic sea. Applied Environmental and Microbiology, vol. 70, No. 8, p. 4971-4979, 2004.*
Cai et al. Application of quantitative real-time reverse transcription-PCR in assessing drug efficacy against the intracellular pathogen cryptosporidium parvum in vitro. Antimicrobial Agents and Chemotherapy, vol. 49(11), p. 4437-4442, 2005.*
Centurion-Lara, et al.,"Detection of Treponema pallidum by a Sensitive Reverse Transcriptase PCR", Journal of Clinical Microbiology, vol. 35, No. 6, pp. 1348-1352, 1997.
Gabrielle M. E. Van Der Vliet, et al., "Assessment of Mycobacterial Viability by RNA Amplification", Antimicrobial Agents and Chemotherapy, American Society for Microbiology, vol. 38, No. 9, XP000601921, Sep. 1994, pp. 1959-1965.
"Bacterial 16S rRNA sequence #10.", Database Geneseqn [Online], XP002549227, (retrieved from EBI accession No. GSN:ADW08254), (Database accession No. ADW08254), Mar. 10, 2005, 1 page.
Database WPI Week 200479, Thomson Scientific, XP002549228.
Bjarne Munk Hansen, et al., "Polymerase chain reaction assay for the detection of Bacillus cereus group cells", Elsevier, FEMS Microbiology Letters, vol. 202, No. 2, XP002984212, Aug. 21, 2001, pp. 209-213.
Kazunori Matsuda, et al., "Sensitive Quantitative Detection of Commensal Bacteria by rRNA-Targeted Reverse Transcription-PCR▼", Applied and Environmental Microbiology, vol. 73, No. 1, American Society for Microbiology, XP002549226, Oct. 2007, pp. 32-39.

L. I. Patrushev, "Artificial genetic systems", "Genetic and protein engineering", vol. 1, Moscow Nauka, 2004, pp. 211-212, 223-233, (with partial English translation).
John L. McKillip et al., "Real-Time Nucleic Acid-Based Detection Methods for Pathogenic Bacteria in Food", J Food Prot, vol. 67, No. 4:823-832 (2004).
Yasuo Saito, et al., "Monitoring the Cell Number and Viability of Lactobacillus helveticus GCL1001 in Human Feces by PCR Methods", FEMS Microbiology Letters. vol. 231:125-130 (2004).
John L. McKillip, et al., "rRNA Stability in Heat-Killed and UV-Irradiated Enterotoxigenic *Staphylococcus aureus* and *Escherichia coli* O157:H7", Appl. Environ. Microbiol., vol. 64, No. 11:4264-4268 (1998).
John L. McKillip, et al., "rRNA Stability in Heat-Killed and UV-Irradiated Enterotoxigenic *Staphylococcus aureus* and *Escherichia coli* O157:H7", Applied and Environmental Microbiology, Nov. 1998, pp. 4264-4268.
Office Action as received in the corresponding Japanese Patent Application No. 2007-500631 dated Apr. 3, 2012 w/English translation of relevant portions.
Office Action as received in the corresponding Korean Patent Application No. 10-2007-7017768 dated Oct. 25, 2013.
Nabil Ben Omar, et al., "Quantification of *Enterococcus faecalis* and *Enterococcus faecium* in different foods using rRNA-targeted oligonucleotide probes", Journal of Microbiological Methods, 61 (2005) 187-192.
Takahiro Matsuki, et al., "Use of 16S rRNA Gene-Targeted Group-Specific Primers for Real-Time PCR Analysis of Predominant Bacteria in Human Feces" Appl. Environ. Microbiol., 2004, 70(12):7220-7228.
Heidy Eleaume, et al., "Comparison of two standardization methods in real-time quantitative RT-PCR to follow *Staphylococcus aureus* genes expression during in vitro growth", Journal of Microbiological Methods, 59 (2004) 363-370.
Combined Office Action and Search Report dated Sep. 2, 2015 in Chinese Patent Application No. 201410452701.9 (with English translation and English translation of Category of Cited Documents).

\* cited by examiner

METHOD OF QUANTITATIVELY ANALYZING MICROORGANISM TARGETING RRNA

CROSS-REFERENCE TO RELATED APPLICATIONS

The present application is a 35 U.S.C. § 371 National Stage patent application of International patent application PCT/JP2006/301467, filed on Jan. 30, 2006, which claims priority to Japanese patent application JP 2005-023448, filed on Jan. 31, 2005.

TECHNICAL FIELD

The present invention relates to a method of quantitating or detecting a microorganism, particularly in a live state, targeting rRNA.

BACKGROUND ART

As a method of quantitating a microorganism, there have been conventionally mainly used a method involving culturing a microorganism in a preliminarily estimated selection medium and measuring the number of microbial cells and a method involving culturing a microorganism in a liquid selection medium and measuring the optical density or absorbance. The following methods have also been used for the identification operation for a microorganism needed in detecting the microorganism in a specimen, for example, a method involving identification thereof through morphologic observation, Gram staining, and microbiological characteristics such as oxygen requirement, sugar-assimilating properties and growing condition in a medium; a method involving determination thereof by a DNA-DNA homology test; and a detection method using a monoclonal antibody to a microbial surface antigen. However, these methods require time and skill and therefore have presented a problem from a standpoint of rapidity and simplicity.

In recent years, gene amplification methods including a PCR method have been used in a wide range of fields as techniques for detecting traces of nucleic acids. These methods have advantages capable of leading to speed-up and simplification, including no mandatory requirement for culturing a microorganism contained in a specimen and capability of directly handling a specimen as a sample. Thus, the methods have been subjected to the investigation of application to the quantitation and detection of a microorganism.

As an example where the PCR method has been applied to the analysis of a microorganism, a method is known for quantitating a bacterium by a PCR method which uses the total DNA as a target sequence and universal primers (Patent Document 1). Methods using 16S rDNA as a target have also been achieved. Known examples thereof include a method for quantitative analysis by a PCR method using 16S rDNA as a target sequence (Patent Document 2), a method for analysis of an intestinal bacteria by a PCR method using 16S rDNA as a target sequence (Patent Document 3), and a method for detection of a bacterial strain of the genus *Lactobacillus*, a bacterium causing turbidity of beer (Patent Document 4). However, these methods have had a problem that they cannot be used as alternatives to a conventional method which has been conventionally employed because detection sensitivity is not achieved to the extent obtained with the culture method. By way of example, performing the method for quantitative analysis as disclosed in Patent Document 2 requires a large amount of template DNA corresponding to a microbial count of $10^5/\mu l$ or more, which makes the method impractical. The low detection sensitivity is probably due to the low number of copies (amount of template), of the total DNA or 16S rDNA providing as a template for the PCR in the microorganism. Since DNA is known to remain even after the dying-out of a microorganism, these methods only quantitate and detect dead and live microorganisms together, which also has posed a problem that they are difficult to precisely quantitate and detect a microorganism in a live state (Non-patent Document 1).

As examples of application of a PCR method to the analysis of a microorganism, attempts have also been made to perform methods using mRNA as a target sequence; known examples thereof include quantitative analysis of a lactic acid bacterium in feces, employing mRNA as a target sequence (Non-patent Document 2). Methods for detecting cancer cells are also known which use as target sequences mRNAs specific to cancer cells in specimens (Patent Documents 5 and 6). However, even these methods have not provided detection sensitivity to the extent that they can replace the conventional method as quantitation methods. Specifically, the detection limit of the quantitative analysis as shown in Patent Document 2 is only $10^{3.5}$ or more cells/g of feces; the analysis method has not been able to be used as an alternative to the conventional culture method in view of detection sensitivity. In addition, these methods target mRNAs of genes unique to the microorganisms, and have been unsuitable for detection in a specimen to be tested containing a large variety of microorganisms because of problems such as complicated primer design and reduced specificity.

Accordingly, the development of a method has been awaited which provides detection sensitivity to the same extent as conventional detection methods while being a rapid method using a PCR method or the like and which further can precisely quantitate and detect a microorganism in a live state.

To improve sensitivity, it is possible to change the design of a target so that the target can be present more stably or in more abundance in cells. However, such a stable target is probably unfavorable for the purpose of detecting only a live microorganism, considering that it is suspected to remain long also in a dead cell thereof. Thus, it is not easy to simultaneously achieve the detection of only live cells and sufficiently high detection sensitivity.

Also, it has been known that rRNA accounts for about 85% of the content of RNA in a cell and has a multicopy number and that rRNA is stable compared to mRNA because it forms a complex with protein. rRNA is also reported to be detected for on the order of 48 hours after microbial death (Non-patent Document 3) and therefore has been commonly believed to be unsuitable for detection of a microorganism in a live state (Non-patent Document 1).

Patent Document 1: Japanese Patent Laid-Open No. 2002-238585
Patent Document 2: Japanese Patent Laid-Open No. 2003-259879
Patent Document 3: Japanese Patent Laid-Open No. 2001-112485
Patent Document 4: Japanese Patent Laid-Open No. 10-210980
Patent Document 5: Japanese Patent Laid-Open No. 10-248600
Patent Document 6: International Publication WO 00/17395 pamphlet
Non-patent Document 1: J Food Prot, vol. 67, No. 4: (2004)

Non-patent Document 2: FEMS Microbiology Letters, vol. 231: 125-130 (2004)

Non-patent Document 3: Appl. Environ. Microbiol., vol. 64, No. 11: 4264-4268 (1998)

An object of the present invention is to provide a method of quantitatively analyzing a microorganism, which can achieve detection sensitivity to the extent of being capable of replacing a conventional culture method and more precise detection of the microorganism in a live state.

DISCLOSURE OF THE INVENTION

As a result of intensive studies, the present inventors have found that rRNA (i.e., 5S, 16S, and 23S in bacteria, and 5S, 18S, 26S or 28S in eukaryotic cells), which has been believed to be unsuitable for detecting a live microorganism in terms of stability, can be unexpectedly used as a target to precisely quantitate and detect the number of microbial cells in a live state without incorporation of dead cells thereof and further that using a PCR method in the quantitation and detection can achieve detection sensitivity to the extent of being capable of replacing a conventional method, and the present invention has thereby been accomplished.

Thus, the present invention provides a method of quantitating a microorganism of interest, using as an index the amount of rRNA of the microorganism in a specimen to be tested.

The present invention also provides a method of detecting a microorganism of interest, using as an index the presence of rRNA of the microorganism in a specimen to be tested.

The present invention also provides a nucleic acid fragment used in the above method, wherein the fragment is a nucleic acid fragment containing a base sequence described in one of SEQ ID NOS: 2, 3 and 5 to 28 or a base sequence complementary thereto, or a nucleic acid fragment containing a base sequence homologous thereto and functionally equivalent thereto.

The present invention further provides a kit for performing the above method.

The detection method targeting rRNA according to the present invention can be used to achieve high detection sensitivity compared to that using a conventional target because of the abundant presence of target while also more precisely detecting and quantitating a microorganism in a live state. A PCR method can also be used in the detection to achieve detection sensitivity to the extent of being capable of replacing a conventional culture method. In addition, the method using a PCR method can achieve marked rapidity and simplicity compared to conventional methods such as a culture method. In other words, the method of the present invention can be used to simultaneously achieve high detection sensitivity, more precise quantitation and/or detection of a live organism, and rapidity and simplicity. Thus, the method of the present invention can be used in practical situations where it is required to detect and/or quantitate a microorganism, such as analysis of intestinal flora and detection and/or quantitation of a microorganism living in a specimen derived from a food or an organism.

BEST MODE FOR CARRYING OUT THE INVENTION

Figure 1:
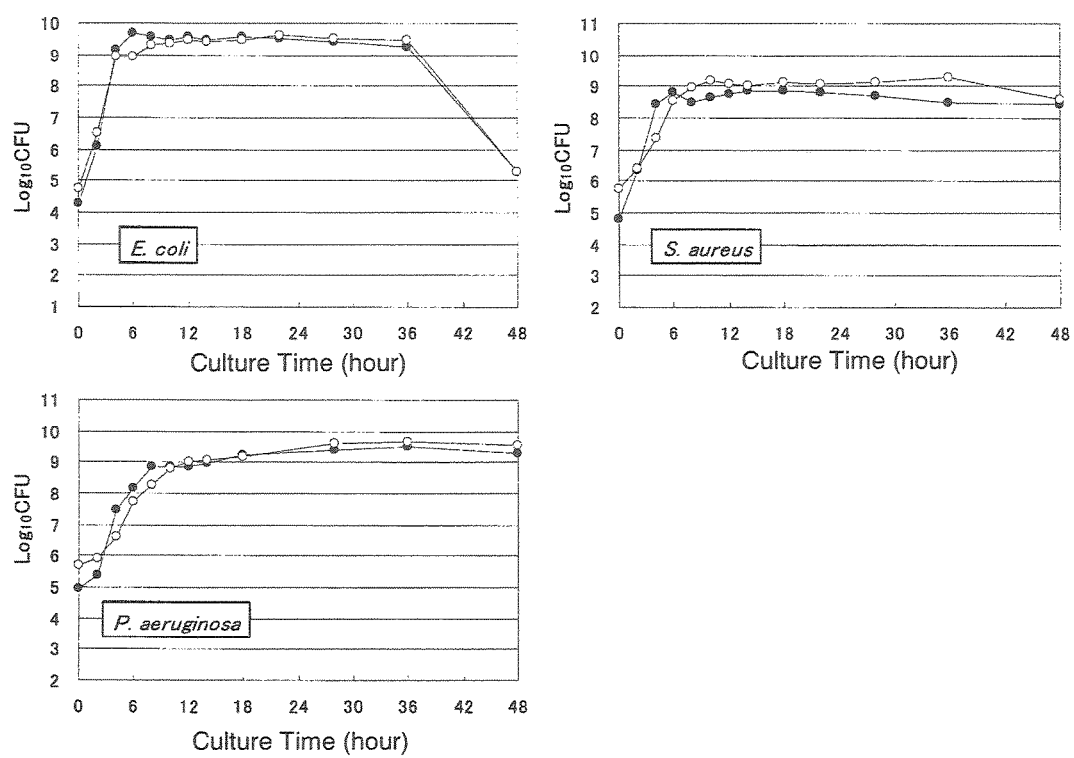
FIG. 1 is a set of graphs showing a correlation between the growth of various microorganisms and the amount of rRNA transcription.

The method of quantitating or detecting a microorganism of interest according to the present invention is characterized by using as an index the abundance or presence of rRNA of the microorganism in a specimen to be tested.

The rRNA of a microorganism of interest refers to an rRNA which a microorganism to be quantitated and detected can have. Examples of the rRNA include prokaryotic 5S, 16S and 23S rRNAs and eukaryotic 5S, 5.8S, 18S, 26S and 28S rRNAs; the 16S, 23S, 18S and 26S rRNAs are particularly preferable in that they are mainly used as reliable indexes for current microbial classification. The microorganism of interest refers to a microorganism to be quantitated and detected, and is not particularly limited. Examples thereof include microorganisms of the family Enterobacteriaceae and the genera *Enterococcus, Lactobacillus, Streptococcus, Staphylococcus, Veillonella, Pseudomonas, Clostridium, Bacteroides, Bifidobacterium, Eubacterium, Prevotella, Ruminococcus, Fusobacterim, Propionibacterium, Peptostreptococcus, Vibrio, Bacillus, Campylobacter, Acinetobacter, Lactococcus, Pediococcus, Weissella, Leuconostoc, Oenococcus, Helicobacter, Neisseria, Listeria, Haemophillus, Mycobacterium, Gardnerella, Legionella, Aeromonas, Moraxella* and *Candida*, and microorganisms as described in Tables 2 and 3 to be mentioned. The microorganism of interest according to the present invention is a concept including not only a microorganism of one strain but also a group, a genus and a family which are each composed of a population of 2 strains or more sharing certain properties.

The specimen to be tested refers to an object which is to be examined for the presence, abundance or the like of a microorganism. Examples of the specimen to be tested include specimens of biological origin such as conjunctival swab, dental calculus, dental plaque, expectorated sputum, throat swab, saliva, nasal discharge, bronchioalveolar lavage, pleural effusion, gastric juice, gastric lavage, urine, cervical mucus, vaginal discharge, skin lesion, feces, blood, ascites fluid, tissue, spinal fluid, synovial fluid, and lesion lavage; and objects potentially containing microorganisms, such as food, medicine, cosmetics, intermediate processed products of food, medicine and cosmetics, microbial broth, plants, soil, activated sludge, and drainage water. The sample of a specimen to be tested refers to a sample taken or prepared from a specimen to be tested, and is not particularly limited provided that it is a sample capable of reflecting the presence or abundance of a microorganism in the specimen. Examples thereof include a mixture containing nucleotides and a mixture containing RNAs contained in a specimen to be tested; preferred is the mixture containing RNAs contained in a specimen to be tested in view of using a PCR method.

The sample of a specimen to be tested can be properly obtained, for example, from the whole or part of a specimen to be tested by a known method, if necessary, after pretreatment using extraction, separation and purification methods. By way of example, the mixture containing RNAs can be obtained, for example, by extraction using a universal method such as "a guanidine-cesium chloride ultracentrifugal method", "an acid guanidine-phenol chloroform (AGPC) method", "a magnetic bead method", and "a silica column method", if necessary, after pretreatment employing a known method such as filtration, centrifugation, and chromatography; a commercial kit (e.g., QIAGEN RNeasy Kit, TRIZOL) may also be used therefor.

The sample of a specimen to be tested used is preferably RNAs in a state stabilized in a microorganism in view of preventing decomposition thereof to maintain high detection sensitivity. The stabilization may be carried out using, for example, a commercial stabilization agent (e.g., RNAprotect Bacterial Reagent, RNAlater). The stabilization is preferably performed immediately after collecting the specimen in view of avoiding a change in the amount of RNAs in the microorganism.

The quantitation of a microorganism of interest according to the present invention uses as an index the amount of rRNA of the microorganism in a specimen to be tested. Here, the amount of rRNA of a microorganism of interest in a specimen to be tested can be determined, for example, by (1) getting the amount of the product amplified by a PCR method using nucleic acid fragments capable of specifically hybridizing to the rRNA of the microorganism of interest and a sample of the specimen, (2) getting the efficiency of hybridization between the nucleic acid fragments capable of specifically hybridizing to the rRNA of the microorganism of interest and a sample of the specimen, or (3) using a quantitative method employing another known method.

Here, in the case (1) of using a PCR method, "the nucleic acid fragments capable of specifically hybridizing to the rRNA of a microorganism of interest" can be designed by comparing the base sequence of the microorganism with the base sequences of other microorganisms to select sequences specific to rRNA which the microorganism of interest can have. Here, the sequence of the rRNA which the microorganism can have can be obtained, for example, by checking against a database (DDBJ, GenBank, etc.). Also, the base sequences can be aligned using software (e.g., Clustal X) to find specific sequences by a visual or any other methods. The sequences specific to a microorganism of interest are preferably selected considering the wideness of a scope in which the microorganism(s) to be quantitated is included. Specifically, for example, if a strain is to be specifically quantitated, sequences specific to the strain are preferably selected; if a genus is to be specifically quantitated, sequences specific to the genus are preferably selected. The selection can be properly performed using a known method.

In addition to the sequences thus designed, the nucleic acid fragments capable of hybridizing to the rRNA of the microorganism of interest can be each properly postulated if based on known technical common knowledge; a base sequence complementary to the aforementioned base sequence, a base sequence homologous thereto similarly usable for quantitating a microorganism of interest, and the like may also be employed. Examples of the homologous base sequence include a nucleic acid fragment containing (a) the aforementioned base sequence which further contains substitution, addition or deletion of one or several, preferably 1 to 10 bases, (b) a base sequence having a sequence identity of 90% or more, preferably 95% or more, more preferably 99% or more with the aforementioned base sequence, or (c) a base sequence capable of hybridizing under stringent conditions to a DNA containing a base sequence complementary to the aforementioned base sequence.

The nucleic acid fragment may also be a part of the nucleic acid fragment to which preferably 100 bases, more preferably 20 bases, still more preferably 10 bases or less are added at both or one end, preferably 5' end, thereof.

The length of the nucleic acid fragment is not particularly limited; however, the fragment preferably comprises 5 to 50, more preferably 12 to 35 bases.

The nucleic acid fragment thus designed can be artificially synthesized, for example, on a DNA synthesizer according to the base sequence thereof. The fragment is preferably that whose specificity has been verified. Here, the specificity can be verified, for example, by confirming that the use of rRNA of interest as a template provides a specific PCR amplified product when compared to a suitable control.

Examples of the nucleic acid fragment include nucleic acid fragments containing the base sequences described in SEQ ID NOS: 1 to 30 or base sequences complementary thereto, or nucleic acid fragments containing base sequences homologous thereto and functionally equivalent thereto. Here, examples of the nucleic acid fragments containing base sequences homologous thereto and functionally equivalent thereto include nucleic acid fragments as shown in (a) to (c) below, which can be used for the quantitation and detection of rRNA of a microorganism of interest.

(a) A nucleic acid fragment containing the base sequence represented by one of SEQ ID NOS: 1 to 30 or a base sequence complementary thereto, wherein the fragment contains deletion, substitution or addition of one or several bases.

(b) A nucleic acid fragment having a sequence identity of 90% or more, preferably 95% or more, more preferably 99% or more with the base sequence represented by one of SEQ ID NOS: 1 to 30 or a base sequence complementary thereto.

(c) A nucleic acid fragment containing a base sequence capable of hybridizing in stringent conditions to DNA containing the base sequence represented by one of SEQ ID NOS: 1 to 30 or a base sequence complementary thereto.

Here, the identity of base sequences is calculated using the homology search program GENETYX®.

"Stringent conditions" include, for example, conditions of keeping, for hybridization, at 42° C. for 16 to 24 hours in a solution containing 50% formamide, 5×SSC, 5×Denhardt's solution, and 250 mg/mL salmon sperm DNA.

The nucleic acid fragment usable for quantitation and detection of rRNA of a microorganism of interest can be obtained, for example, by performing a PCR method to select a nucleic acid fragment which provides an amplification product when the rRNA of the microorganism is used as a template while not providing the product when another target, e.g., rRNA of a different microorganism or mRNA, is employed as a template.

Then, (1) a nucleic acid fragment containing the base sequence described in SEQ ID NO: 1 or 2 or a base sequence complementary thereto, or a nucleic acid fragment containing a base sequence homologous thereto and functionally equivalent thereto can be used for specifically quantitating and detecting *Bacillus cereus;* (2) a nucleic acid fragment containing the base sequence described in SEQ ID NO: 3 or 4 or a base sequence complementary thereto, or a nucleic acid fragment containing a base sequence homologous thereto and functionally equivalent thereto can be used for specifically quantitating and detecting *Clostridium perfrin-*

*gens*; (3) a nucleic acid fragment containing the base sequence described in SEQ ID NO: 5 or 6 or a base sequence complementary thereto, or a nucleic acid fragment containing a base sequence homologous thereto and functionally equivalent thereto can be used for specifically quantitating and detecting Enterobacteriaceae; (4) a nucleic acid fragment containing the base sequence described in SEQ ID NO: 7 or 8 or a base sequence complementary thereto, or a nucleic acid fragment containing a base sequence homologous thereto and functionally equivalent thereto can be used for specifically quantitating and detecting the genus *Staphylococcus*; (5) a nucleic acid fragment containing the base sequence described in SEQ ID NO: 9 or 10 or a base sequence complementary thereto, or a nucleic acid fragment containing a base sequence homologous thereto and functionally equivalent thereto can be used for specifically quantitating and detecting the genus *Pseudomonas*; (6) a nucleic acid fragment containing the base sequence described in SEQ ID NO: 11 or 12 or a base sequence complementary thereto, or a nucleic acid fragment containing a base sequence homologous thereto and functionally equivalent thereto can be used for specifically quantitating and detecting the genus *Enterococcus*; (7) a nucleic acid fragment containing the base sequence described in SEQ ID NO: 13 or 14 or a base sequence complementary thereto, or a nucleic acid fragment containing a base sequence homologous thereto and functionally equivalent thereto can be used for specifically quantitating and detecting the *Lactobacillus acidophilus* subgroup; (8) a nucleic acid fragment containing the base sequence described in SEQ ID NO: 15 or 16 or a base sequence complementary thereto, or a nucleic acid fragment containing a base sequence homologous thereto and functionally equivalent thereto can be used for specifically quantitating and detecting the *Lactobacillus ruminis* subgroup; (9) a nucleic acid fragment containing the base sequence described in SEQ ID NO: 17 or 18 or a base sequence complementary thereto, or a nucleic acid fragment containing a base sequence homologous thereto and functionally equivalent thereto can be used for specifically quantitating and detecting the *Lactobacillus plantarum* subgroup; (10) a nucleic acid fragment containing the base sequence described in SEQ ID NO: 19 or 20 or a base sequence complementary thereto, or a nucleic acid fragment containing a base sequence homologous thereto and functionally equivalent thereto can be used for specifically quantitating and detecting the *Lactobacillus reuteri* subgroup; (11) a nucleic acid fragment containing the base sequence described in SEQ ID NO: 21 or 22 or a base sequence complementary thereto, or a nucleic acid fragment containing a base sequence homologous thereto and functionally equivalent thereto can be used for specifically quantitating and detecting the *Lactobacillus sakei* subgroup; (12) a nucleic acid fragment containing the base sequence described in SEQ ID NO: 23 or 24 or a base sequence complementary thereto, or a nucleic acid fragment containing a base sequence homologous thereto and functionally equivalent thereto can be used for specifically quantitating and detecting the *Lactobacillus casei* subgroup; (13) a nucleic acid fragment containing the base sequence described in SEQ ID NO: 25 or 26 or a base sequence complementary thereto, or a nucleic acid fragment containing a base sequence homologous thereto and functionally equivalent thereto can be used for specifically quantitating and detecting *Lactobacillus brevis*; (14) a nucleic acid fragment containing the base sequence described in SEQ ID NO: 27 or 28 or a base sequence complementary thereto, or a nucleic acid fragment containing a base sequence homologous thereto and functionally equivalent thereto can be used for specifically quantitating and detecting *Lactobacillus fructivorans*; and (15) a nucleic acid fragment containing the base sequence described in SEQ ID NO: 29 or 30 or a base sequence complementary thereto, or a nucleic acid fragment containing a base sequence homologous thereto and functionally equivalent thereto can be used specifically quantitating and detecting *Lactobacillus fermentum*.

Here, the nucleic acid fragment containing the base sequence in SEQ ID NO: 1 is a known nucleic acid fragment as described in FEMS Microbiology Letters, vol. 202: 209-213 (2001). The nucleic acid fragment containing the base sequence in SEQ ID NO: 4 is a known nucleic acid fragment as described in Microbiol. Immunol., vol. 46, No. 5: 353-358 (2002) The nucleic acid fragment containing the base sequence in SEQ ID NO: 29 or 30 is a known nucleic acid fragment as described in Japanese Patent Laid-Open No. 11-151097. In contrast, the nucleic acid fragments containing the base sequences described in SEQ ID NOS: 2, 3 and 5 to 28 are nucleic acid fragments found by the present inventors.

The PCR method using the nucleic acid fragments thus prepared and a sample of a specimen to be tested can be performed by "PCR in a reaction system containing the sample, using the nucleic acid fragments as primers and the rRNA of a microorganism of interest as a template". The PCR method is not particularly limited provided that the reaction specifically amplifies a nucleotide fragment derived from rRNA of a microorganism of interest. Preferred is a method including the step of using rRNA of the microorganism of interest as a template to prepare cDNA employing an enzyme, preferably a reverse transcriptase, or the like. More preferred is a method including, in addition to the above step, the step of using the cDNA thus prepared as a template to amplify the nucleotide fragment. The PCR method may be carried out using, for example, a known RT-PCR. Here, the RT-PCR may be performed using a known method such as two-step RT-PCR and one-step RT-PCR; however, the one-step RT-PCR is preferable in that it is particularly simple and prevents cross-contamination.

The one-step RT-PCR method may be carried out using, for example, a commercial kit (e.g., QIAGEN One-Step RT-PCR kit). The enzyme having a transcription activity which may be used in the RT reaction may be any of various reverse transcriptases such as M-MHV reverse transcriptase. The DNA polymerase used in the PCR amplifying DNA preferably has a heat resistance to a temperature of 90° C. or more.

The PCR may be conducted by performing one to several cycles of a thermal denaturation reaction for converting double-stranded DNA into single-stranded DNA, an annealing reaction for hybridizing primers to template cDNA and an extension reaction for allowing DNA polymerase to act, under temperature conditions of 90 to 98° C., 37 to 72° C. and 50 to 75° C., respectively. A preferable example of reaction conditions is thermal denaturation at 95° C. for 30 seconds, annealing at 60° C. for 30 seconds, and extension at 72° C. for 60 seconds.

For the PCR, two types of primers are preferably used as a set. Here, the two primers are needed to be made to form a combination of a leading strand and a lagging strand. The nucleic acid fragments provided by the present invention are each set to have an approximately constant annealing temperature in the RT-PCR, which enables nucleic acid fragments of a plurality of microorganisms to be tested simultaneously. The nucleic acid fragment of the present invention can also be used as a probe, and may also be employed in combination with a different known universal primer, oligonucleotide or the like.

The sample of a specimen to be tested containing rRNA providing a template for the RT-PCR preferably has a total content of RNAs of 1 pg to 1 µg, more preferably 10 pg to 0.1 µg.

When the PCR is appropriately conducted, a correlation typically exists among "the amount of PCR-amplified product", "the number of PCR cycles", and "the amount of template for PCR". Thus, the amount of rRNA of a microorganism of interest can be determined if calculation is properly performed considering the amount of the amplified product formed by the PCR thus conducted and the number of the PCR cycles.

As shown in FIG. 1 of Example to be described, it has been demonstrated that a good correlation also exists between "the amount of rRNA of the microorganism of interest" thus determined and "the number of cells of the microorganism of interest". The number of cells of the microorganism of interest can therefore be determined if calculation is performed considering "the amount of rRNA of the microorganism of interest" thus determined. Without undergoing the process of calculating "the amount of rRNA of the microorganism of interest", the number of cells of the microorganism of interest can be determined even by proper calculation considering "the amount of the amplified product formed by the PCR" and "the number of the PCR cycles" obtained as described above.

The amount of PCR-amplified product and the number of PCR cycles can be learned by any method without particular limitation, for example, by identifying the number of PCR cycles when the DNA reaches a certain arbitrarily chosen amount. The identification can be performed, for example, by using "a PCR method including labeling a PCR product in combination with a PCR method including measuring the label with time" to identify the number of PCR cycles when a certain chosen fluorescence intensity is reached. Here, the certain fluorescence intensity is preferably chosen "within the range which the intensity can reach when the amplification product is logarithmically increased" in terms of reflecting an appropriate correlation therebetween. The range can be properly understood using a known method. Here, examples of the labeling include labeling with a fluorescent dye; examples of the measurement of the label include the measurement of the fluorescence intensity. Here, examples of the labeling with the fluorescent dye include labeling with an intercalating fluorescent dye. Examples of the intercalating fluorescent dye include SYBR®Green I. The intercalating dye has a property in which the fluorescence intensity is enhanced by the intercalation thereof into a double-stranded nucleic acid, thereby resulting in the emitting of a fluorescence having an intensity reflecting the amount of an amplified PCR product. The labeling with a fluorescent dye can also be performed by use of a TaqMan probe, Molecular Beacon or the like labeled with the fluorescent dye. The TaqMan probe or Molecular Beacon is a probe in which a fluorescent dye and a quencher are bound to an oligonucleotide homologous to an internal sequence of a region amplified by PCR, and is used by allowing to coexist in a PCR system. The interaction of the fluorescent dye and quencher bound to the probe allows the emitting of fluorescence in response to a PCR amplification reaction, thereby enabling an amplified PCR product to be observed with time by measuring fluorescence intensity at each PCR stage. However, the TaqMan probe, Molecular Beacon, or the like makes it necessary to pick out a microbe-specific complementary sequence suitable for the probe, which may be difficult depending on an object.

The amount of rRNA can be determined by considering "the amount of PCR-amplified product and the number of PCR cycles" thus learned and the results of a suitable comparative experiment. Specifically, the amount of rRNA of the microorganism of interest can be calculated using a known method, for example, by considering "the results of the comparative experiment performed employing an rRNA whose amount is known" to properly contrast therewith "the amount of PCR-amplified product and the number of PCR cycles" learned as described above.

Then, the number of cells of a microorganism of interest can be determined by considering "the amount of rRNA of the microorganism" thus calculated and the results of a suitable comparative experiment. Specifically, the number of cells of the microorganism of interest can be calculated using a known method, for example, by considering "the results of the comparative experiment performed employing a sample of a specimen to be tested in which the number of cells of the corresponding microorganism is known" to properly contrast therewith "the amount of rRNA of the microorganism of interest" thus calculated. In the contrast, in view of simplicity, a standard curve is preferably used which shows a correlation between "the number of cells of the microorganism of interest" used as a template for PCR and "the number of PCR cycles" when the certain amount of PCR-amplified product is reached (hereinafter sometimes referred to as $C_T$ value). The standard curve is typically prepared by plotting the $C_T$ value against the number of cells of a targeted microorganism (see FIG. 2). The microorganism used for preparing the standard curve may be a known strain such as the type strain thereof.

Without undergoing the process of specifically calculating the amount of rRNA, the number of cells of the microorganism of interest can also be directly calculated by properly contrasting "the results of a comparative experiment performed using a sample of a specimen to be tested, in which the number of cells of the corresponding microorganism is known" with "the amount of PCR-amplified product and the number of PCR cycles" learned as described above. Specifically, the $C_T$ value derived from the sample of the specimen to be tested may be applied to the above-described standard curve.

As described above, the amount of rRNA of a microorganism of interest in a specimen to be tested can also be determined, for example, by (2) learning the efficiency of hybridization between a nucleic acid fragment capable of specifically hybridizing to the rRNA of the microorganism of interest and a sample of the specimen to be tested.

Here, the nucleic acid fragment capable of specifically hybridizing to the rRNA of the microorganism of interest, which may be used is, for example, ones designed and prepared as described above. The nucleic acid fragment is preferably a labeled nucleic acid fragment. Here, examples of the label include an enzyme, a paramagnetic ion, biotin, a fluorescent dye, a chromophore, a heavy metal, and a radioisotope; more preferred examples of the marker include an enzyme. Here, examples of the enzyme include horseradish peroxidase and alkaline phosphatase. The labeling can be carried out by a known method.

The amount of rRNA of a microorganism of interest in a specimen to be tested and/or the number of cells of the microorganism can be learned using a known conversion method by measuring the extent of hybridization between a sample of the specimen to be tested and the nucleic acid fragment. The method of measuring the extent of the hybridization is not particularly limited and may be carried out according to a known method; for example, it may be performed by measuring the label added to the nucleic acid fragment. Specifically, for example, the method can be carried out by measuring fluorescence intensity when using the nucleic acid fragment labeled with a fluorescent dye. The measurement is preferably performed in parallel with measurement using a suitable control. Here, examples of the suitable control include "a sample known not to specifically hybridize to the nucleic acid fragment used", "a sample derived from a specimen to be tested where the specimen contains an already known number of cells of a microorganism of interest", and "a sample taken or prepared from a specimen to be tested where the specimen contains an already known amount of rRNA of a microorganism of interest". By checking against the control, the RNA amount or cell number of the microorganism of interest can be learned using a known conversion method. The number of cells of the microorganism of interest can also be learned using a known method by considering the amount of rRNA of the microorganism of interest thus calculated and the results of a suitable comparative experiment.

The method of detecting a microorganism of interest according to the present invention uses as an index the presence of rRNA of the microorganism in a sample of a specimen to be tested. Here, the term "detecting a microorganism" includes identifying the microorganism. The term also includes determining the presence of a microorganism to be detected in a specimen or the absence of a microorganism to be detected in a specimen.

To determine the presence of rRNA of a microorganism of interest in a specimen to be tested using the detection method of the present invention, the detection described in (1), (2), or (3) below may be carried out, for example.

(1) Detecting a product amplified by PCR using a nucleic acid fragment capable of specifically hybridizing to the rRNA of the microorganism of interest and a sample of the specimen to be tested.

(2) Detecting the hybridization between the nucleic acid fragment and the sample.

(3) Detecting the rRNA of the microorganism using a different known method.

The methods (1) to (3) can be easily performed by considering the previously described methods. The presence of rRNA of the microorganism of interest indicates that the microorganism has been present in the specimen to be tested, which enables the detection of the microorganism. However, the detection is preferably carried out by comparison with a suitable control because non-specific amplification of PCR product and non-specific hybridization can occur.

As shown in Examples described later, it has been demonstrated that high detection sensitivity can be achieved by the quantitative method using the amount of rRNA as an index and the detection method using the presence of rRNA as an index compared to that by conventional methods using the amount of rDNA as an index. As shown in Examples to be described, it has also been demonstrated that the method using the amount of rRNA as an index can accurately quantitate and detect a microorganism in a live state without quantitating and detecting dead cells in conjunction therewith.

Thus, the use of the quantitation or detection method of the present invention (hereinafter, also referred to as "the method of the present invention") enables a microorganism to be specifically quantitated and detected at higher detection sensitivity than that for conventional methods and even in a live state thereof. Consequently, the method of the present invention can be used, for example, in applications described in (1) to (4) below.

(1) An application in which a microorganism of interest contained in a specimen to be tested is quantitated and detected in a live sate at higher detection sensitivity than that for conventional methods.

(2) An application in which the number of dead cells of a microorganism contained in a specimen to be tested is quantitated and detected at higher detection sensitivity than that for conventional methods.

(3) An application in which the ratio of the numbers of dead and live cells of a microorganism is measured at higher detection sensitivity than that for conventional methods.

(4) An application in which the presence or abundance of a live microorganism is "determined" at higher detection sensitivity than that for conventional methods.

Here, the determination includes, for example, (a) quantitation and detection for ascertaining the presence or abundance of a live microorganism when the number of cells of the live microorganism is needed to be more accurately and precisely ascertained and (b) when "the number of cells of a live microorganism" has been calculated in another experimental system, determination for examining the accuracy of the experiment and the preciseness of the numerical values calculated. In this respect, when the number of dead cells is quantitated, the measurement of the total number of the dead cells and the live cells is preferably performed in conjunction therewith, for example, by a method known to detect the dead cells together with the live cells. The number of the dead cells can be determined by subtracting the number of the live cells calculated by the method of the present invention from the total number.

The method of the present invention can also be used as a method for quantitating or detecting a microorganism difficult to measure by conventional methods, such as a microorganism incapable of forming colonies and a microorganism incapable of liquid culture.

As shown in Examples described later, it has been demonstrated that the use of a PCR method in the quantitation and detection method can achieve detection sensitivity to the same extent as a culture method. Thus, the method of the present invention can also be used as a method of quantitating or detecting a microorganism at detection sensitivity to the same extent or more as the culture method, i.e., at a detection sensitivity of $10^0$ cells or more/g of specimen or $10^0$ cells or more/mL of specimen.

A microorganism can also be very rapidly and simply quantitated or detected when the PCR method is used, compared to the culture method. In addition, according to the method using the PCR method, the process from the extraction of RNA from a specimen to the quantitation or detection of the microorganism can be completed within about 6 hours. Thus, the method of the present invention can also be used as a method capable of detecting a microorganism in a short period of time (within 6 hours).

The use of the method using a PCR method according to the present invention can simultaneously achieve high detection sensitivity, more accurate quantitation and detection of a live microorganism, and rapidity and simplicity. Thus, the method of the present invention can be used, for example, in the application of "the examination of contaminant and hazardous bacteria, pathogenic microorganisms, or the like" in medical site and food industry where rapid and sensitive quantitation or detection is particularly required.

The method of the present invention can also be carried out using a kit for performing the method. Here, examples of the kit for performing the method include a kit containing (1) nucleic acid fragments capable of specifically hybridizing to rRNA of a microorganism of interest, (2) a protocol in which an implementation method is described, and/or (3) a reagent used for extraction of RNA, stabilization of RNA, and/or a PCR. However, the kit of the present invention is not limited thereto, and refers to a collection of all or part of requisites for performing all or part of the steps of the method. Here, "requisites for performing the steps" can be properly understood by considering the description set forth in this specification.

EXAMPLES

The content of the present invention is described below in further detail by way of Examples. However, the invention is not intended to be limited thereto.

Example 1

Preparation of Primers

For various bacterial strains, 16S and 23S rRNA DNA sequences were obtained from the DNA Data Bank of Japan. These sequences were aligned using the Clustal W program, followed by preparing a phylogenetic tree. The strains were classified by family, genus and subgroup on a basis of the phylogenetic tree; primers were designed for each classification. The sequences of the primers prepared and the rRNA species of interest are shown in Table 1. References in which the sequences are described are shown in the column for "references" in Table 1. If the column is blank, this indicates that the sequence is a novel sequence found by the present invention. In this respect, Non-patent Document 4 represents Microbiol. Immunol., vol. 46, No. 5: 353-358 (2002); Non-patent Document 5, FEMS Microbiology Letters, vol. 202, 209-213 (2001); and Patent Document 7, Japanese Patent Laid-Open No. 11-151097.

TABLE 1

| SEQ ID NOS: | Targets | | Names of Primers | Sequences | Sizes of Amplification Products (bp) | References |
|---|---|---|---|---|---|---|
| 1 | Bacillus cereus | 16S rRNA | S-S-Bc-200-a-S18 | TCGAAATTGAAAGGCGGC | 285 | Non-patent Document 5 |
| 2 | | | Bc2R | CCAGCTTATTCAACTAGCACTT | | |
| 3 | Clostridium perfringens | 16S rRNA | s-Clper-F | GGGGGTTTCAACACCTCC | 170 | Non-patent Document 4 |
| 4 | | | ClPER-R | GCAAGGGATGTCAAGTGT | | |
| 5 | Enterobacteriaceae | 23S rRNA | En-lsu 3F | TGCCGTAACTTCGGGAGAAGGCA | 428 | |
| 6 | | | En-lsu 3'R | TCAAGGACCAGTGTTCAGTGTC | | |
| 7 | Staphylococcus | 16S rRNA | g-Staph-F | TTTGGGCTACACACGTGCTACAATGGACAA | 79 | |
| 8 | | | g-Staph-R | AACAACTTTATGGGATTTGCWTGA | | |
| 9 | Pseudomonas | 16S rRNA | PSD7F | CAAAACTACTGAGCTAGAGTACG | 215 | |
| 10 | | | PSD7R | TAAGATCTCAAGGATCCCAACGGCT | | |
| 11 | Enterococcus | 16S rRNA | g-Encoc-F | ATCAGAGGGGGATAACACTT | 336 | |
| 12 | | | g-Encoc-R | ACTCTCATCCTTGTTCTTCTC | | |
| 13 | Lactobacillus acidophilus subgroup | 16S rRNA | sg-Laci-F | GATGCATAGCCGAGTTGAGACACTGAT | 197 | |
| 14 | | | sg-Laci-R | TAAAGGCCAGTTACTACCTCTATCC | | |
| 15 | Lactobacillus ruminis subgroup | 16S rRNA | sg-Lrum-F | CACCGAATGCTTGCAYTCA | 182 | |
| 16 | | | sg-Lrum-R | GCCGCGGGTCCATCCAAAA | | |
| 17 | Lactobacillus plantarum subgroup | 16S rRNA | sg-Lpla-F | CTCTGGTATTGATTGGTGCTTGCAT | 54 | |
| 18 | | | sg-Lpla-R | GTTCGCCACTCACTCAAATGTAAA | | |
| 19 | Lactobacillus reuteri subgroup | 16S rRNA | sg-Lreu-F | GAACGCAYTGGCCCAA | 290 | |
| 20 | | | sg-Lreu-R | TCCATTGTGGCCGATCAGT | | |
| 21 | Lactobacillus sakei subgroup | 16S rRNA | sg-Lsak-F | CATAAAACCTAMCACCGCATGG | 303 | |
| 22 | | | sg-Lsak-R | TCAGTTACTATCAGATACRTTCTTCTC | | |
| 23 | Lactobacillus casei subgroup | 16S rRNA | sg-Lcas-F | ACCGCATGGTTCTTGGC | 296 | |
| 24 | | | sg-Lcas-R | CCGACAACAGTTACTCTGCC | | |
| 25 | Lactobacillus brevis | 16S rRNA | s-Lbre-F | ATTTTGTTTGAAAGGTGGCTTCGG | 289 | |
| 26 | | | s-Lbre-R | ACCCTTGAACAGTTACTCTCAAAGG | | |
| 27 | Lactobacillus fructivorans | 16S rRNA | s-Lfru-F | TGCGCCTAATGATAGTTGA | 452 | Patent Document 7 |
| 28 | | | s-Lfru-R | GATACCGTCGCGACGTGAG | | |
| 29 | Lactobacillus fermentum | 16S rRNA | Lfer-1 | CCTGATTGATTTTGGTCGCCAAC | 414 | Patent Document 7 |
| 30 | | | Lfer-2 | ACGTATGAACAGTTACTCTCATACGT | | |

W = A, T: Y = C, T: M = A, C: R = A, G

Example 2

Determination of the Specificity of Primers

To determine whether the primers of Example 1 actually have specificity or not, they were examined for specificity to various bacteria. Specifically, 50 µl of each of various bacterial cultures as shown in Table 2 (57 species in 28 genera) and Table 3 (60 species in 18 genera) was added in a 2-fold volume of RNAprotect Bacterial Reagent (QIAGEN) and incubated at room temperature for 5 minutes. The suspension was then centrifuged at 5,000 g for 10 minutes and subjected to the removal of the supernatant. Thereto were added 450 µl of bacteriolytic buffer (346.5 µl of RLT buffer (QIAGEN), 3.5 µl of β-mercaptoethanol, 100 µl of TE buffer) and 300 mg of glass beads (0.1 mm in diameter), which was then vigorously mixed by the FastPrep FP120 (Bio 101) at 5,000 rpm for one minute to crush the bacterial cells. To the crush solution was added 500 µl of water-saturated phenol, which was then incubated at 60° C. for 10 minutes. Thereto was added 100 µl of chloroform/isoamyl alcohol (CIA), which was mixed and then subjected to a centrifugation at 12,000 rpm for 5 minutes at 4° C. To the recovered supernatant was added an equal volume of water-saturated phenol/chloroform, which was then mixed and again subjected to a centrifugation under the same conditions. To the recovered supernatant was added an equal volume of CIA, which was then shaken and again subjected to a centrifugation under the same conditions. To 400 µl of the recovered supernatant were added an equal volume of isopropyl alcohol and a ⅒-fold volume of 3M sodium acetate, which was mixed by inversion and then subjected to a centrifugation at 15,000 rpm for 10 minutes at 4° C. The resultant was subjected to the removal of the supernatant, to which 500 µl of 75% ethanol was added before mixing by inversion, followed by subjecting the mixture to a centrifugation at 15,000 rpm for 2 minutes at 4° C. After removing the supernatant and air-drying the inside of the tube, the precipitate was dissolved in 50 µl of RNase-free water to make a total RNA extract. A quantitative RT-PCR was performed using QIAGEN One-Step RT-PCR Kit (QIAGEN). The composition of the reaction solution (total volume: 25 µl) was: 2 µl of the total RNA solution (equivalent to $2 \times 10^5$ CFU); and 1× QIAGEN One-Step RT-PCR Buffer, 0.5 mM dNTP Mix, a ¹⁄₂₅-fold volume of QIAGEN One-Step RT-PCR Enzyme Mix, a ¹⁄₁₀₀,₀₀₀-fold volume of SYBR® Green I (from Molecular Probes) and 0.75 µM (each) primers (described in Table 1) which were adjusted so that the respective amounts form final concentrations. RNA equivalent to $2 \times 10^5$ CFU was used as a template in the RT-PCR. The reaction solution was first subjected to a reverse transcription reaction at 50° C. for 30 minutes, and then heated at 95° C. for 15 minutes to inactivate the reverse transcriptase. Subsequently, 40 to 45 cycles of 94° C. for 20 seconds, 55° C. or 60° C. for 20 seconds and 72° C. for 50 seconds were performed to measure the amount of an amplification product as a fluorescence intensity of SYBR® Green I for each cycle. These series of reactions were performed using the ABI PRISM® 7900HT system (from Applied Biosystems).

As a result, as shown in Table 2, it was demonstrated that only a bacterial genus or strain of interest can be specifically detected by the primer En-lsu 3F/3'R (Enterobacteriaceae), g-Staph-F/R (the genus *Staphylococcus*), PSD7F/R (the genus *Pseudomonas*), s-Clper-F/ClPER-R (*Clostridium perfringens*), S-S-Bc-200-a-S-18/Bc2R (*Bacillus cereus*) or g-Encoc F/R (the genus *Enterococcus*). In addition, as set out in Table 3, it was shown that only a subgroup or strain of interest can be specifically detected by the primer sg-Laci-F/R (*Lactobacillus acidophilus* subgroup), sg-Lsak-F/R (*Lactobacillus sakei* subgroup), sg-Lcas-F/R (*Lactobacillus casei* subgroup), sg-Lrum-F/R (*Lactobacillus ruminis* subgroup), sg-Lreu-F/R (*Lactobacillus reuteri* subgroup), sg-Lpla-F/R (*Lactobacillus plantarum* subgroup), s-Lbre-F/R (*Lactobacillus brevis*), s-Lfru-F/R (*Lactobacillus fructivorans*) or LFer-1/2 (*Lactobacillus fermentum*). In Tables 2 and 3, + indicates that specific detection was able to be achieved ($C_T$ value: 1 to 30); − indicates that the $C_T$ value was 31 or more or that no amplification product was obtained.

TABLE 2

| | Reactions with the following primers | | | | | |
|---|---|---|---|---|---|---|
| Target | En-lsu 3F/3'R | g-Encoc-F/R | g-Staph-F/R | s-Clper-F/ClPER-R | S-S-Bc-200-a-S-18/BC2R | PSD7F/R |
| *Escherichia coli* | + | − | − | − | − | − |
| *Citrobacter freundii* | + | − | − | − | − | − |
| *Citrobacter koseri* | + | − | − | − | − | − |
| *Citrobacter amalonaticus* | + | − | − | − | − | − |
| *Enterobacter cloacae* | + | − | − | − | − | − |
| *Enterobacter aerogenes* | + | − | − | − | − | − |
| *Enterobacter sakazakii* | + | − | − | − | − | − |
| *Enterobacter cancerogenus* | + | − | − | − | − | − |
| *Enterobacter amnigenus* | + | − | − | − | − | − |
| *Klebsiella pneumoniae* | + | − | − | − | − | − |
| *Klebsiella oxytoca* | + | − | − | − | − | − |
| *Serratia marcescens* | + | − | − | − | − | − |
| *Proteus mirabilis* | + | − | − | − | − | − |
| *Proteus vulgaris* | + | − | − | − | − | − |
| *Proteus penneri* | + | − | − | − | − | − |
| *Hafnia alvei* | + | − | − | − | − | − |
| *Edwardsiella tarda* | + | − | − | − | − | − |
| *Providencia alcalifaciens* | + | − | − | − | − | − |
| *Providencia rettgeri* | + | − | − | − | − | − |
| *Morganella morganii* | + | − | − | − | − | − |
| *Salmonella choleraesuis* | + | − | − | − | − | − |
| *Yersinia enterocolitica* | + | − | − | − | − | − |
| *Pseudomonas aeruginosa* | − | − | − | − | − | + |
| *Pseudomonas fluorescens* | − | − | − | − | − | + |

TABLE 2-continued

| Target | Reactions with the following primers | | | | | |
|---|---|---|---|---|---|---|
| | En-lsu 3F/3'R | g-Encoc-F/R | g-Staph-F/R | s-Clper-F/ClPER-R | S-S-Bc-200-a-S-18/BC2R | PSD7F/R |
| *Pseudomonas putida* | − | − | − | − | − | + |
| *Acinatebacter calcoaceticus* | − | − | − | − | − | − |
| *Bacteroides ovatus* | − | − | − | − | − | − |
| *Bacteroides vulgatus* | − | − | − | − | − | − |
| *Prevotella melaninogenica* | − | − | − | − | − | − |
| *Collinsella aerofaciens* | − | − | − | − | − | − |
| *Eggerthella lenta* | − | − | − | − | − | − |
| *Bifidobacterium catenulatum* | − | − | − | − | − | − |
| *Bifidobacterium longum* | − | − | − | − | − | − |
| *Ruminococcus productus* | − | − | − | − | − | − |
| *Ruminococcus obeum* | − | − | − | − | − | − |
| *Clostridium orbisciendens* | − | − | − | − | − | − |
| *Clostridium perfringens* | − | − | − | + | − | − |
| *Streptococcus intermedius* | − | − | − | − | − | − |
| *Streptococcus bovis* | − | − | − | − | − | − |
| *Staphylococcus aureus* | − | − | + | − | − | − |
| *Staphylococcus epidermidis* | − | − | + | − | − | − |
| *Staphylococcus haemolyticus* | − | − | + | − | − | − |
| *Staphylococcus lugdunensis* | − | − | + | − | − | − |
| *Staphylococcus saprophyticus* | − | − | + | − | − | − |
| *Staphylococcus schleiferi ss. coagulans* | − | − | + | − | − | − |
| *Bacillus cereus* | − | − | − | − | + | − |
| *Bacillus subtilis* | − | − | − | − | − | − |
| *Enterococcus faecalis* | − | + | − | − | − | − |
| *Enterococcus faecium* | − | + | − | − | − | − |
| *Enterococcus hirae* | − | + | − | − | − | − |
| *Enterococcus gallinarum* | − | + | − | − | − | − |
| *Enterococcus flavescens* | − | + | − | − | − | − |
| *Enterococcus durans* | − | + | − | − | − | − |
| *Lactobacillus acidophilus* | − | − | − | − | − | − |
| *Lactobacillus casei* | − | − | − | − | − | − |
| *Campylobacter jejuni* | − | − | − | − | − | − |
| *Candida albicans* | − | − | − | − | − | − |

TABLE 3

| Target | Reactions with the following primers | | | | | | | | |
|---|---|---|---|---|---|---|---|---|---|
| | sg-Laci-F/R | sg-Lsak-F/R | sg-Lcas-F/R | sg-Lrum-F/R | sg-Lreu-F/R | sg-Lpla-F/R | s-Lbre-F/R | s-Lfru-F/R | Lfer-1/2 |
| *Lactobacillus acidophilus* | + | − | − | − | − | − | − | − | − |
| *Lactobacillus gasseri* | + | − | − | − | − | − | − | − | − |
| *Lactobacillus crispatus* | + | − | − | − | − | − | − | − | − |
| *Lactobacillus jensenii* | + | − | − | − | − | − | − | − | − |
| *Lactobacillus helveticus* | + | − | − | − | − | − | − | − | − |
| *Lactobacillus johnsonii* | + | − | − | − | − | − | − | − | − |
| *Lactobacillus delburueckii ss. delburueckii* | + | − | − | − | − | − | − | − | − |
| *Lactobacillus delburueckii ss. lactis* | + | − | − | − | − | − | − | − | − |
| *Lactobacillus delburueckii ss. bulgaricus* | + | − | − | − | − | − | − | − | − |
| *Lactobacillus amylovorus* | + | − | − | − | − | − | − | − | − |
| *Lactobacillus gallinarum* | + | − | − | − | − | − | − | − | − |
| *Lactobacillus intestinalis* | + | − | − | − | − | − | − | − | − |
| *Lactobacillus hamsteri* | − | + | − | − | − | − | − | − | − |
| *Lactobacillus sakei* | − | + | − | − | − | − | − | − | − |
| *Lactobacillus curvatus* | − | + | − | − | − | − | − | − | − |
| *Lactobacillus vitulinus* | − | + | − | − | − | − | − | − | − |
| *Lactobacillus graminis* | − | + | − | − | − | − | − | − | − |
| *Lactobacillus casei* | − | − | + | − | − | − | − | − | − |
| *Lactobacillus rhamnosus* | − | − | + | − | − | − | − | − | − |
| *Lactobacillus zeae* | − | − | + | − | − | − | − | − | − |
| *Lactobacillus ruminis* | − | − | − | + | − | − | − | − | − |
| *Lactobacillus murinus* | − | − | − | + | − | − | − | − | − |
| *Lactobacillus salivarius ss. salivarius* | − | − | − | + | − | − | − | − | − |
| *Lactbacillus salivarius ss. salicinius* | − | − | − | + | − | − | − | − | − |
| *Lactobacillus animalis* | − | − | − | + | − | − | − | − | − |
| *Lactobacillus mali* | − | − | − | + | − | − | − | − | − |
| *Lactobacillus reuteri* | − | − | − | − | + | − | − | − | − |
| *Lactobacillus vaginalis* | − | − | − | − | + | − | − | − | − |

TABLE 3-continued

| | Reactions with the following primers | | | | | | | | |
|---|---|---|---|---|---|---|---|---|---|
| Target | sg-Laci-F/R | sg-Lsak-F/R | sg-Lcas-F/R | sg-Lrum-F/R | sg-Lreu-F/R | sg-Lpla-F/R | s-Lbre-F/R | s-Lfru-F/R | Lfer-1/2 |
| Lactobacillus oris | − | − | − | − | + | − | − | − | − |
| Lactobacillus panis | − | − | − | − | + | − | − | − | − |
| Lactobacillus plantarum | − | − | − | − | − | + | − | − | − |
| Lactobacillus pentosus | − | − | − | − | − | + | − | − | − |
| Lactobacillus brevis | − | − | − | − | − | − | + | − | − |
| Lactobacillus fructivorans | − | − | − | − | − | − | − | + | − |
| Lactobacillus fermentum | − | − | − | − | − | − | − | − | + |
| Escherichia coli | − | − | − | − | − | − | − | − | − |
| Pseudomonas aeruginosa | − | − | − | − | − | − | − | − | − |
| Pseudomonas fluorescens | − | − | − | − | − | − | − | − | − |
| Pseudomonas putida | − | − | − | − | − | − | − | − | − |
| Acinatebacter calcoaceticus | − | − | − | − | − | − | − | − | − |
| Bacteroides ovatus | − | − | − | − | − | − | − | − | − |
| Bacteroides vulgatus | − | − | − | − | − | − | − | − | − |
| Prevotella melaninogenica | − | − | − | − | − | − | − | − | − |
| Collinsella aerofaciens | − | − | − | − | − | − | − | − | − |
| Eggerthella lenta | − | − | − | − | − | − | − | − | − |
| Bifidobacterium catenulatum | − | − | − | − | − | − | − | − | − |
| Bifidobacterium longum | − | − | − | − | − | − | − | − | − |
| Ruminococcus productus | − | − | − | − | − | − | − | − | − |
| Ruminococcus obeum | − | − | − | − | − | − | − | − | − |
| Clostridium orbiscindens | − | − | − | − | − | − | − | − | − |
| Clostridium perfringens | − | − | − | − | − | − | − | − | − |
| Streptococcus intermedius | − | − | − | − | − | − | − | − | − |
| Streptococcus bovis | − | − | − | − | − | − | − | − | − |
| Staphylococcus aureus | − | − | − | − | − | − | − | − | − |
| Bacillus cereus | − | − | − | − | − | − | − | − | − |
| Bacillus subtilis | − | − | − | − | − | − | − | − | − |
| Enterococcus faecalis | − | − | − | − | − | − | − | − | − |
| Lactococcus lactis lactis | − | − | − | − | − | − | − | − | − |
| Campylobacter jejuni | − | − | − | − | − | − | − | − | − |
| Candida albicans | − | − | − | − | − | − | − | − | − |

Example 3

Examination of a Relationship Between the Growth Status of Various Microorganisms and the Amount of rRNA Transcription Using *Escherichia coli*, *S. aureus* and *P. aeruginosa* cells of different culture phases, a relation was examined between the number of live bacterial cells measured using a culture method and the number of bacterial cells having the ability to form colonies, derived from the amount of rRNA transcription measured by a quantitative RT-PCR method. Specifically, after the start of aerobic culture of each bacterium with shaking at 37° C. in BHI medium, the bacterial cultures were collected with time, followed by using the cultures to measure the number of bacterial cells by a culture method employing BHI agar medium (37° C., 24 hours). On the other hand, RNA was extracted from samples similarly collected and subjected to quantitative RT-PCR analysis. The number of bacterial cells in each sample was calculated on a basis of the standard curve prepared in the manner described in Example 4, using RNA extracted from a bacterial strain in the late logarithmic growth phase, the number of which cells was known. In this respect, the total RNA extraction and quantitative RT-PCR were performed as described in Example 2. The results are shown in FIG. 1. In FIG. 1, the black circle (●) indicates the number of bacterial cells calculated from the amount of rRNA transcription, and the white circle (○), the number of bacterial cells determined by the culture method. For all of the bacterial strains subjected to analysis, from the logarithmic growth phase to the death phase, a strong relationship was observed between the variation curves of the number of live bacterial cells determined by the culture method in the bacterial solution and the number of bacterial cells calculated from the amount of rRNA transcription. This demonstrated that the number of cells of a live microorganism could be determined under any condition by measuring the amount of rRNA transcription.

Example 4

Preparation of Standard Curves and Comparison with a Quantitative PCR Method

Standard curves were prepared by the method of the present invention (quantitative RT-PCR method) using cultured cells, in the late logarithmic growth phase, of *P. aeruginosa* YIT6108$^T$ (type strain) and *S. aureus* YIT6075$^T$ (type strain). Standard curves were also prepared by a quantitative PCR method to compare with those prepared by the method of the present invention. Axenic cells of each strain cultured in BHI medium were separated so as to provide cell numbers of $10^5$, $10^4$, $10^3$, $10^2$, $10^1$ and $10^0$, and subjected to RNA extraction as described in Example 2. The extracts were each subjected to quantitative RT-PCR according to Example 2 using primers as described in Table 1. A correlation was examined between the resultant $C_T$ value and the number of the cells determined by the culture method described in Example 3. Using a method described below, DNAs obtained from the same samples were also each examined for the quantitation thereof by a PCR method employing rDNA as a target sequence. Specifically, 1 mL of PBS was added to each of the bacterial solutions separated so as to provide cell numbers of $10^5$, $10^4$, $10^3$, $10^2$, $10^1$ and $10^0$, which was stirred and then centrifuged at 15,000 rpm at 5 minutes for 4° C., followed by removing the supernatant.

An operation was repeated twice in which 1 mL of PBS was added to the precipitate, which was then stirred and centrifuged before removing the supernatant. To the resultant pellet were added 300 µl of bacteriolytic buffer (100 mM Tris-HCl, 40 mM EDTA, 1% SDS, pH: 9.0), 500 µl of TE-saturated phenol, and 300 mg of glass beads (0.1 mm in diameter), which was then vigorously shaken in the FastPrep FP120 at 5,000 rpm for 30 seconds to crush the bacterial cells. The crush solution was centrifuged under conditions of 15,000 rpm, 4° C. and 5 minutes, followed by recovering the supernatant. Phenol (TE-saturated)/chloroform/isoamyl alcohol was added to the supernatant, which was vigorously shaken in the FastPrep FP120 at 4,000 rpm for 45 seconds and then subjected to a centrifugation operation under conditions of 15,000 rpm, 4° C. and 5 minutes. Alcohol precipitation was performed using the separated and recovered supernatant, followed by dissolving the precipitate in 50 µl of TE buffer to make a DNA solution. Subsequently, a PCR was conducted using the resultant DNA solution as a template. The PCR was performed in a total 25 µl of a reaction solution containing 2 µl of the DNA solution and 10 mM Tris-HCl (pH 8.3), 50 mM KCl, 2.5 mM $MgCl_2$, 0.45% Triton X-100, 200 µM dNTP mixture, a 1/100,000-fold volume of SYBR® Green I, 11 ng/µl TaqStart® antibody (from ClonTech), 0.05 U/µl Taq DNA polymerase (from Takara) and 0.25 µM (each) primers (PSD7F/R or g-Staph-F/R) as final concentrations. The reaction solution was heated at 94° C. for 5 minutes, then subjected to 40 cycles of 94° C. for 20 seconds, 60° C. for 20 seconds and 72° C. for 50 seconds, and subsequently reacted at 72° C. for 10 minutes. The amount of the amplification product was measured for each cycle as a fluorescence intensity of SYBR® Green I. These series of reactions were carried out using ABI PRISM®7900HT. In this respect, 1/25 the extraction amount of each of RNA and DNA was subjected to the reaction.

Figure 2:
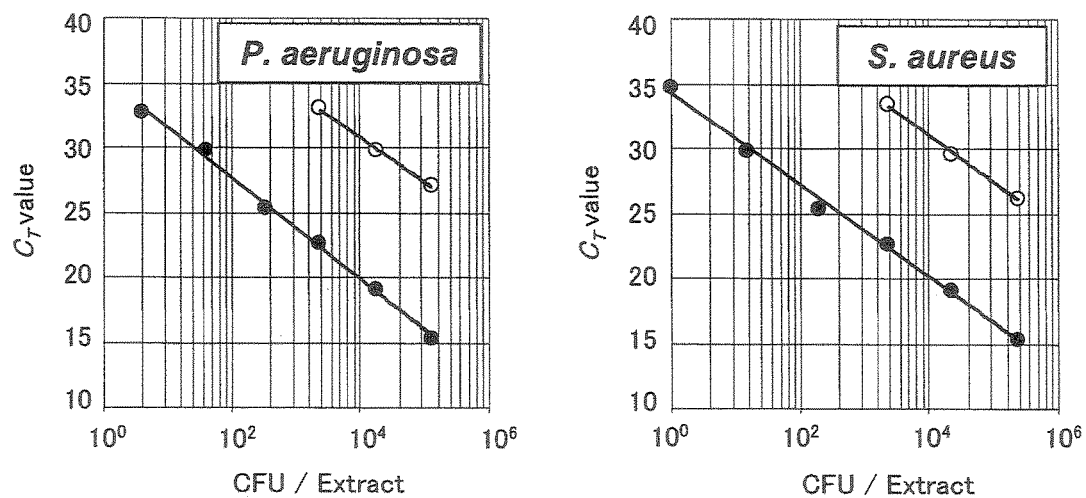
FIG. 2 is a set of graphs each showing a standard curve obtained by a quantitative RT-PCR method and comparison of the range of detection between the method and a quantitative PCR method.

As a result, as shown in FIG. 2, both of the methods showed an extremely good correlation between the logarithmic number of bacterial cells and the $C_T$ value. In FIG. 2, the $C_T$ value is plotted against the number of cells/extract measured by the culture method for each bacterial strain serving as a sample. The black circle (●) indicates the case of the quantitative RT-PCR, and the white circle (○), the case of the quantitative PCR. In the approximate curve obtained through the quantitative RT-PCR method, the correlation coefficient ($R^2$-value) was 0.9955 for *P. aeruginosa* and 0.9961 for *S. aureus*. This demonstrated that the standard curves enable the calculation of the number of bacterial cells from the $C_T$ values. In addition, the quantitative RT-PCR method was able to detect $10^0$ bacterial cell in the samples, indicating that the method had a detection sensitivity comparable with a conventionally used culture method. This demonstrated that the method could be used for the quantitation or detection of a microorganism as an alternative to the culture method. The method of the present invention had a detection sensitivity about 1,000 times that of the PCR method using rDNA as a target sequence, demonstrating that it had a marked detection sensitivity as compared to a previously studied means for quantitating a microorganism using a gene amplification method.

Example 5

Quantitative Detection of a Bacterium in Feces

Various concentrations of *P. aeruginosa* were each added to human feces to compare the detection range of a quantitative PCR method with that of the method of the present invention. *P. aeruginosa*-added fecal samples were prepared in each of which cells of *P. aeruginosa* equivalent to $10^1$, $10^2$, $10^3$, $10^4$, $10^5$, $10^6$, $10^7$ or $10^8$ cells per 20 mg of human feces were added. The total RNA was extracted from each of the *P. aeruginosa*-added fecal samples and used as a template to perform the quantitative RT-PCR of the present invention. DNA was also extracted from each of the same samples and used as a template to perform the quantitative PCR. In addition, the same samples are subjected to the measurement of the number of bacterial cells using a culture method. The extraction of the total RNA and the quantitative RT-PCR method were carried out as described in Example 2; the culture method, as in Example 3; and the extraction of DNA and the quantitative PCR method, as in Example 4. In this respect, 1/2,500 the amounts of the total RNA and total DNA obtained were subjected to the quantitative RT-PCR and the quantitative PCR, respectively.

Figure 3:
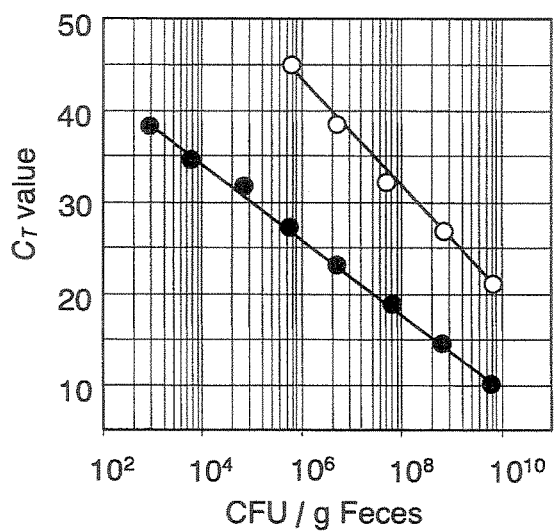
FIG. 3 is a graph showing the range of detection of *P. aeruginosa* from human feces.

As a result, as shown in FIG. 3, the method of the present invention showed linearity in an approximate curve obtained from measurements in the range of $10^{2.9}$ to $10^{10}$ cells/g of feces in the *P. aeruginosa*-added fecal samples. In FIG. 3, the $C_T$ value is plotted against the number of cells/g of feces measured by the culture method for *P. aeruginosa* serving as a sample. The black circle (●) indicates the case of the quantitative RT-PCR, and the white circle (○), the case of the quantitative PCR. In the human feces, the quantitative limit of the method of the present invention was $10^{2.9}$ cells or more/g of feces, and was nearly comparable to that of the culture method, which was $10^2$ cells or more/g of feces. The culture method took one day, while the method of the present invention was completed from the stabilization of RNA of the specimen to the quantitation in about 6 hours. On the other hand, in analysis by the quantitative PCR method, linearity was observed in an approximate curve obtained from measurements in the range of $10^{5.8}$ to $10^{10}$ cells/g of feces, and the detection limit was about 1,000 times lower than that of the quantitative RT-PCR method.

Example 6

Analysis of Human Fecal Enterobacteriaceae by Quantitative RT-PCR and a Culture Method Human fecal flora was analyzed by a quantitative RT-PCR using the enterobacteriaceae-specific primers En-lsu 3F/3'R. Fresh excreted feces were collected from 38 adults and diluted by 1/10 under anaerobic conditions with a transport medium (10% glycerin, 5% cysteine, 1% lab lemco powder, 0.045% NaCl, 0.0225% $KH_2PO_4$, 0.0225% $K_2HPO_4$, 0.0225% $(NH_4)_2SO_4$, 0.00225% $CaCl_2$, 0.00225% $MgSO_4$). A 200 µl of aliquot (20 mg as feces) was taken from the diluent and subjected to the extraction of total RNA using a quantitative RT-PCR method. The quantitative RT-PCR was carried out using 1/2,500 the amount of the total RNA as a template. An aliquot of the same diluent was also subjected to the quantitation of CFU by a culture method (DHL selection medium). The stabilization of RNA, the extraction of the total RNA, and the quantitative RT-PCR were according to Example 2, and the culture method was in accordance with a conventional method. The total RNA extracted from *E. coli* YIT 6044$^T$ (type strain) was used for preparing a standard curve for calculating the number of bacterial cells by the quantitative RT-PCR.

Figure 4:
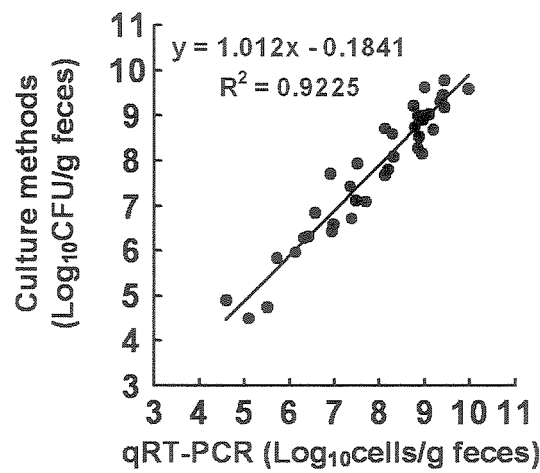
FIG. 4 is a graph showing comparison of quantitative values for human fecal enterobacteriaceae when determined by a quantitative RT-PCR method and by a culture method.

As a result, as shown in FIG. 4, it was demonstrated that the quantitative RT-PCR method targeting rRNA according to the present invention and the culture method showed an extremely strong correlation (correlation coefficient:

0.9255). In FIG. 4, the ordinate represents the results of quantitation by the culture method, and the abscissa represents the results of quantitation by the method of the present invention. For the culture method, it took 2 days to accomplish all operations, while for the method of the present invention, all operations were completed in about 6 hours.

Example 7

Examining Microorganisms in Cow's Milk

Various concentrations of E. coli, S. aureus, and B. cereus were each added to commercial cow's milk to compare the quantitative value of a pour plate culture method with that of the method of the present invention. E. coli or S. aureus was added to the commercial cow's milk so as to provide microbial numbers of $10^0$, $10^1$, $10^2$, $10^3$, $10^4$, $10^5$, and $10^6$ per mL to make samples. Of each sample, 1 mL was subjected to the extraction of total RNA, and 1 mL to the pour plate culture method (E. coli: desoxycholate agar medium, S. aureus and B. cereus: conventional agar medium, 37° C., 20±2 hours). The total RNA extracted was analyzed by a quantitative RT-PCR method using primers as described in Table 1 to determine a correlation between the resultant $C_T$ value and the number of microbial cells obtained by the pour plate culture method. In this respect, the total RNA extraction and the quantitative RT-PCR method were performed by the method described in Example 2; ¹⁄₂₅ the amount of the total RNA extracted was subjected to the quantitative RT-PCR.

Figure 5:
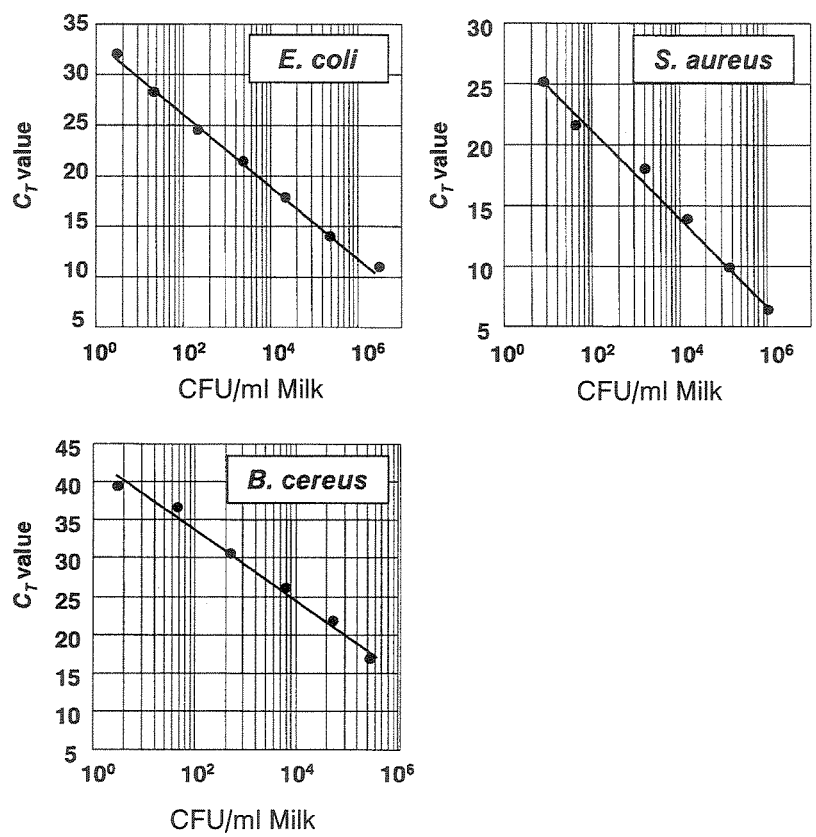
FIG. 5 is a set of graphs showing the sensitivity of detection of *E. coli, S. aureus*, and *B. cereus* from cow's milk.

As a result, as shown in FIG. 5, the $C_T$ value was correlated with the number of microbial cells in the range of $10^0$ to $10^6$ cells per ml of the milk for any of the strains. In FIG. 5, the $C_T$ value is plotted against the number of cells/mL of the milk measured by the pour plate culture method for quantitating E. coli (upper left of FIG. 5), S. aureus (upper right of FIG. 5) and B. cereus (lower left of FIG. 5) serving as a sample. The quantitative limit of the method of the present invention was $10^0$ cell or more/mL of the milk and was comparable to that of the pour plate culture method. This demonstrated that the method of the present invention could provide an alternative to a pour plate culture method using the official culture medium (desoxycholate agar medium or conventional agar medium) as described in the Ministerial ordinance concerning compositional standard, etc. for milk and milk products. In addition, the pour plate culture method took one day, while the method of the present invention was completed from the stabilization of RNA of the specimen to the quantitation in about 6 hours.

Example 8

Examining Bacteria in Blood

Various concentrations of S. aureus or P. aeruginosa were each added to human blood to compare the quantitative value of a pour plate culture method (blood culture method) with that of the method of the present invention. S. aureus or P. aeruginosa was added, so as to provide bacterial numbers of $10^0$, $10^1$, $10^2$, $10^3$, $10^4$, and $10^5$ per mL, to the human blood to which a ¹⁄₁₀-fold volume of a 3.8% sodium citrate solution was added as an anticoagulant to make samples. Of each sample, 0.5 mL was subjected to the extraction of total RNA, and 0.5 mL to the pour plate culture method (BHI agar medium). The total RNA extracted was analyzed by a quantitative RT-PCR method to determine a correlation between the resultant $C_T$ value and the number of bacterial cells obtained by the pour plate culture method. The total RNA extraction and the quantitative RT-PCR method were performed by the method described in Example 2. In this respect, ¹⁄₂₅ the amount of the total RNA extracted was subjected to the quantitative RT-PCR.

Figure 6:
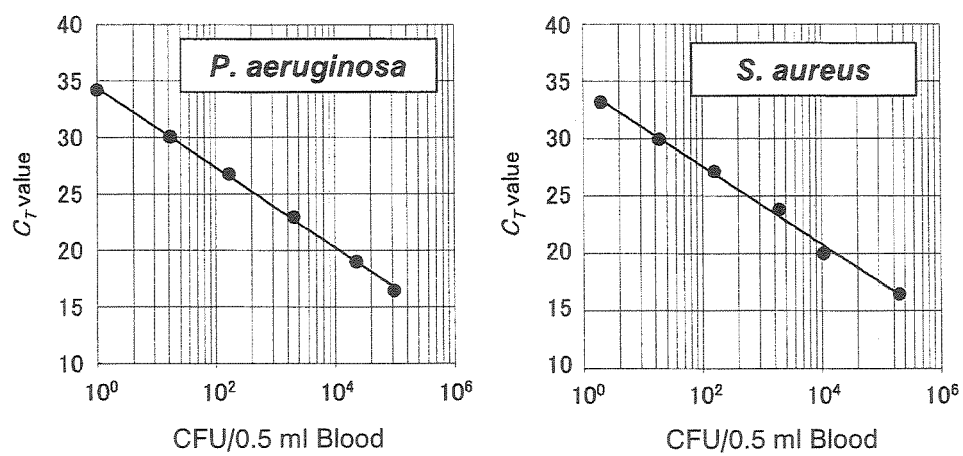
FIG. 6 is a set of graphs showing the sensitivity of detection of *P. aeruginosa* and *S. aureus* from blood.

As a result, as shown in FIG. 6, the number of bacterial cells was correlated with the $C_T$ value in the range of $10^0$ to $10^5$ cells/0.5 ml for each of the strains. In FIG. 6, the $C_T$ value is plotted against the number of cells/0.5 mL of the blood measured by the pour plate culture method for quantitating P. aeruginosa (left of FIG. 6) or S. aureus (right of FIG. 6) serving as a sample. The quantitative limit of the method of the present invention was $10^0$ cell or more/0.5 mL of the blood and was comparable to that of the pour plate culture method. This demonstrated that the method of the present invention could provide an alternative to the pour plate culture method. In addition, the pour plate culture method took one day, while the method of the present invention was completed from the stabilization of RNA of the specimen to the quantitation in about 6 hours.

Example 9

Examining E. coli in a Fermented Milk Product

E. coli was added to commercial Yakult (from Yakult Honsha Co., Ltd.) so as to provide bacterial numbers of $10^0$, $10^1$, $10^2$, $10^3$, $10^4$ and $10^5$ per mL to make samples. Of each sample, 1 mL was subjected to the extraction of total RNA, and 1 mL to a pour plate culture method using a desoxycholate agar medium (37° C., 20±2 hours). The total RNA extracted was analyzed by a quantitative RT-PCR method using the enterobacteriaceae-specific primers En-lsu 3F/3'R to examine a correlation between the resultant $C_T$ value and the number of microbial cells obtained by the pour plate culture method. The total RNA extraction was carried out as described in Example 2 except for the crushing of bacterial cells by addition of glass beads and the quantitative RT-PCR method was performed as described in Example 2. In this respect, ¹⁄₂₅ the amount of the total RNA extracted was subjected to the quantitative RT-PCR.

Figure 7:
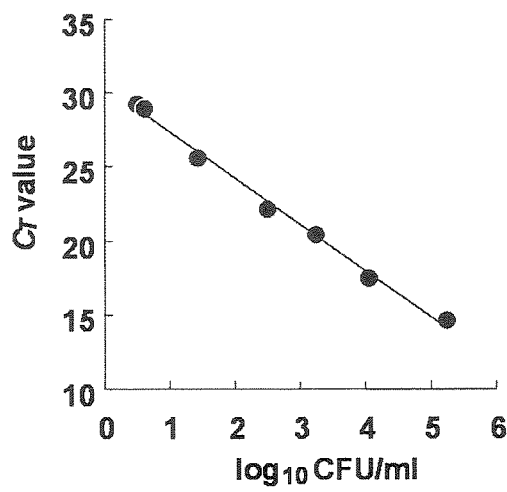
FIG. 7 is a graph showing the sensitivity of detection of *E. coli* from a fermented milk product.

As a result, as shown in FIG. 7, the $C_T$ value was strongly correlated with the number of microbial cells in the range of $10^0$ to $10^5$ cells per mL. In FIG. 7, the $C_T$ value is plotted against the number of $\log_{10}$ cells/mL of Yakult measured by the pour plate culture method for quantitating E. coli serving as a sample. The quantitative limit of the method of the present invention was $10^0$ cell or more/mL of Yakult and was comparable to that of the pour plate culture method. This demonstrated that the method of the present invention could provide an alternative to a pour plate culture method using the official culture medium (desoxycholate agar medium) as described in the Ministerial ordinance concerning compositional standard, etc. for milk and milk products. In addition, the pour plate culture method took one day, while the method of the present invention was completed from the stabilization of RNA of the specimen to the quantitation in about 6 hours.

Example 10

Analysis of Lactobacilli and Enterococci in Human Feces by Quantitative RT-PCR and a Culture Method The cell numbers of bacteria of the genera Lactobacillus and Enterococcus in human feces were compared by a quantitative RT-PCR method using primers as described in Table 1 and by a culture method. Fresh excreted feces were collected from 48 healthy adults, treated using the method described in Example 6, and subjected to RNA stabilization, total RNA extraction and quantitative RT-PCR by the methods described in Example 2. In this respect, 1/2,000 to 1/200,000 the amount of the total RNA obtained was subjected to the quantitative RT-PCR. An aliquot of the same fecal diluent was also subjected to the quantitation of CFU by a culture method (the genus *Lactobacillus*: LBS medium, the genus *Enterococcus*: COBA medium, 37° C. for 48 hours in both cases). The culture method was according to a conventional method; the appearing colonies were subjected to the identification of bacterial species by a biochemical property test (Gram staining, catalase test, API Strep). The cell number of bacteria of the genus *Lactobacillus* by the quantitative RT-PCR method was calculated by combining the cell numbers of bacteria obtained by quantitative RT-PCR methods using the primers sg-Laci-F/R (*Lactobacillus acidophilus* subgroup), sg-Lsak-F/R (*Lactobacillus sakei* subgroup), sg-Lcas-F/R (*Lactobacillus casei* subgroup), sg-Lrum-F/R (*Lactobacillus ruminis* subgroup), sg-Lreu-F/R (*Lactobacillus reuteri* subgroup), sg-Lpla-F/R (*Lactobacillus plantarum* subgroup), s-Lbre-F/R (*Lactobacillus brevis*), s-Lfru-F/R (*Lactobacillus fructivorans*) and LFer-1/2 (*Lactobacillus fermentum*).

As a result, as shown in Table 4, the cell numbers of bacteria of the genus *Lactobacillus* and the genus *Enterococcus* in the human feces were nearly comparable between the method of the present invention and the culture method.

In contrast, detection frequency was high for both genera in the method of the present invention compared to the culture method. This seemed to be due to the following reason: (a) bacteria were present which belonged to the genus *Lactobacillus* or *Enterococcus* now targeted but could not grow because the selection medium had a stronger-than-necessary selectivity; or (b) the weak selectivity of the selection media used led to the growth, in the media, of bacterial genera abundantly present other than the target, which did not enable the detection of the bacterial genera targeted. The above-described results suggested that the method of the present invention not only enables the cell number of bacteria comparable to that by a culture method to be obtained but also can detect or quantitate bacteria which have not previously been able to be detected by the culture method. In addition, for the culture method, it took 7 days to accomplish all operations including the identification of bacterial species, while for the method of the present invention, all operations were completed in about 20 hours.

TABLE 4

| Genus | Quantitative RT-PCR Method | | Culture Method | |
|---|---|---|---|---|
| | $\log_{10}$ cell/g · feces | Frequency (%) | $\log_{10}$ CFU/g · feces | Frequency (%) |
| *Lactobacillus* | 5.2 ± 1.2 | 44/46 (96) | 5.5 ± 1.4 | 37/46 (80) |
| *Enterococcus* | 6.2 ± 1.0 | 46/46 (100) | 6.2 ± 1.9 | 23/46 (50) |

The invention claimed is:

1. A method of quantitating only an amount of live microorganisms in a sample, the method comprising
synthesizing a complementary DNA (cDNA) from total RNA extracted from the microorganisms in the sample to yield ribosomal RNA (rRNA) specific cDNA,
amplifying a target region of only the rRNA from the synthesized cDNA, by a polymerase chain reaction (PCR) in the presence of a fluorescent dye to yield a number of amplified products comprising the fluorescent dye intercalated therein,
measuring the number of amplified products by detecting fluorescence from the intercalated dye to identify the number of PCR cycles when the amplified product reaches a certain amount, and
comparing the number of PCR cycles to a standard curve that correlates the amount of live microorganism cells to PCR cycles to determine the amount of live microorganisms in the sample,
wherein the synthesizing the cDNA and the amplifying the target region are performed by a reverse transcriptase-polymerase chain reaction (RT-PCR)
wherein only the number of amplified products as measured from the number of PCR cycles compared to the standard curve indicates the amount of live microorganisms in the sample,
wherein dead cells are not quantitated in the method, and
wherein the amplifying the rRNA comprises providing a nucleic acid primer pair that can specifically hybridize to the rRNA of the microorganisms, the primer pair being selected from the group consisting of
SEQ ID NO:2 and SEQ ID NO: 3;
SEQ ID NO:5 and SEQ ID NO: 6;
SEQ ID NO:7 and SEQ ID NO: 8;
SEQ ID NO:9 and SEQ ID NO: 10;
SEQ ID NO:11 and SEQ ID NO: 12;
SEQ ID NO:13 and SEQ ID NO: 14;
SEQ ID NO:15 and SEQ ID NO: 16;
SEQ ID NO:17 and SEQ ID NO: 18;
SEQ ID NO:19 and SEQ ID NO: 20;
SEQ ID NO:21 and SEQ ID NO: 22;
SEQ ID NO:23 and SEQ ID NO: 24;
SEQ ID NO:25 and SEQ ID NO: 26;
SEQ ID NO:27 and 28;
and base sequences complementary thereto.

2. The method according to claim 1, wherein the rRNA of the microorganism in the sample is stabilized in the microorganism.

3. The method according to claim 1, wherein the rRNA is 16S rRNA.

4. The method according to claim 1, wherein the standard curve is prepared from RNA extracted from a bacterial strain in the late logarithmic growth phase.

5. The method according to claim 1, wherein the method from total RNA extraction to quantitating is within 6 hours.

6. The method according to claim 1, wherein the quantitating is at a detection sensitivity of $10_0$ cells or more per gram of specimen or $10_0$ cells or more per ml of specimen.

7. The method according to claim 1, wherein the sample is a fecal sample, a blood sample, or a food sample.

8. The method according to claim 1, wherein the sample is a fecal sample.

9. The method according to claim 8, further comprising diluting the fecal sample prior to synthesizing the cDNA.

10. The method according to claim 1, further comprising diluting the sample prior to synthesizing the cDNA.

11. The method according to claim 1, wherein the synthesizing the cDNA and amplifying are performed by a one-step reverse transcriptase polymerase chain reaction (RT-PCR).

12. The method according to claim 1, further comprising performing the reverse transcriptase-polymerase chain reaction (RT-PCR) on at least one control RNA sample selected from the group consisting of a sample known not to be able to specifically be amplified in the reaction, a sample from a specimen to be tested where the specimen contains an already known number of cells of the microorganisms, and a sample from a specimen to be tested where the specimen contains an already known amount of rRNA of the microorganism of interest.

13. The method according to claim 1, wherein the microorganism is one or more selected from the group consisting of *Bacillus cereus, Clostridium perfringens, Enterobacteriaceae*, a microorganism of the genus *Staphylococcus*, a microorganism of the genus *Pseudomonas*, a microorganism of the genus *Enterococcus*, a microorganism of the *Lactobacillus acidophilus* subgroup, a microorganism of the *Lactobacillus ruminis* subgroup, a microorganism of the *Lactobacillus plantarum* subgroup, a microorganism of the *Lactobacillus reuteri* subgroup, a microorganism of the *Lactobacillus sakei* subgroup, a microorganism of the *Lactobacillus casei* subgroup, *Lactobacillus brevis*, and *Lactobacillus fructivorans*.

* * * * *

SEQUENCE LISTING

```
<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgaaattga aaggcggc                                                   18

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagcttatt caactagcac tt                                              22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggggtttca acacctcc                                                   18
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaagggatg tcaagtgt                                                    18

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgccgtaact tcgggagaag gca                                              23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcaaggacca gtgttcagtg tc                                               22

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttgggctac acacgtgcta caatggacaa                                       30

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aacaacttta tgggatttgc wtga                                             24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caaaactact gagctagagt acg                                              23

```
<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taagatctca aggatcccaa cggct                                         25

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcagagggg gataacactt                                               20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actctcatcc ttgttcttct c                                             21

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatgcatagc cgagttgaga gactgat                                       27

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taaaggccag ttactacctc tatcc                                         25

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccgaatgc ttgcaytca                                                19

<210> SEQ ID NO 16
```

<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gccgcgggtc catccaaaa                                               19

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ctctggtatt gattggtgct tgcat                                        25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gttcgccact cactcaaatg taaa                                         24

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gaacgcaytg gcccaa                                                  16

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
tccattgtgg ccgatcagt                                               19

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cataaaacct amcaccgcat gg                                           22

<210> SEQ ID NO 22
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcagttacta tcagatacrt tcttctc                                              27

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
accgcatggt tcttggc                                                         17

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccgacaacag ttactctgcc                                                      20

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
attttgtttg aaaggtggct tcgg                                                 24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acccttgaac agttactctc aaagg                                                25

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgcgcctaat gatagttga                                                       19

<210> SEQ ID NO 28
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 28
gataccgtcg cgacgtgag                                                    19

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cctgattgat tttggtcgcc aac                                               23

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgtatgaac agttactctc atacgt                                            26
```